US010139346B2

(12) United States Patent
Dutertre et al.

(10) Patent No.: US 10,139,346 B2
(45) Date of Patent: Nov. 27, 2018

(54) OPTICAL MICROSCOPY SYSTEM AND METHOD FOR RAMAN SCATTERING WITH ADAPTIVE OPTICS

(71) Applicant: HORIBA JOBIN YVON SAS, Longjumeau (FR)

(72) Inventors: Bertrand Dutertre, Wattrelos (FR); Denis Cattelan, Antony (FR); Emmanuel Fretel, Croix (FR)

(73) Assignee: HORIBA JOBIN YVON SAS, Longjumeau (FR)

( * ) Notice: Subject to any disclaimer, the term of this patent is extended or adjusted under 35 U.S.C. 154(b) by 0 days.

(21) Appl. No.: 15/121,632

(22) PCT Filed: Feb. 24, 2015

(86) PCT No.: PCT/FR2015/050447
§ 371 (c)(1),
(2) Date: Aug. 25, 2016

(87) PCT Pub. No.: WO2015/128579
PCT Pub. Date: Sep. 3, 2015

(65) Prior Publication Data
US 2016/0363538 A1    Dec. 15, 2016

(30) Foreign Application Priority Data
Feb. 27, 2014  (FR) ..................... 14 51597

(51) Int. Cl.
*G01N 21/65*       (2006.01)
*G01J 3/02*        (2006.01)
(Continued)

(52) U.S. Cl.
CPC ............ *G01N 21/65* (2013.01); *G01J 3/0205* (2013.01); *G01J 3/44* (2013.01); *G02B 21/0048* (2013.01);
(Continued)

(58) Field of Classification Search
CPC . G02B 21/16; G02B 21/0076; G02B 21/0064
See application file for complete search history.

(56) References Cited

U.S. PATENT DOCUMENTS

2011/0109903 A1*  5/2011 Lee ..................... G01J 3/02
                                             356/303
2013/0278744 A1* 10/2013 Debarre ............. G02B 21/06
                                             348/79

OTHER PUBLICATIONS

John M. Girkin, Simon P. Poland, Amanda J. Wright, Christian Freudiger, Conor L. Evans, X. Sunney Xie, "Adaptive optics applied to coherent anti-Stokes Raman scattering microscopy", Proc. SPIE 6860, Multiphoton Microscopy in the Biomedical Sciences VIII, 68600T (Feb. 15, 2008).*

(Continued)

*Primary Examiner* — Dominic J Bologna
(74) *Attorney, Agent, or Firm* — Young & Thompson

(57) ABSTRACT

An optical apparatus for Raman scattering microscopy includes a laser source that emits a laser beam at an excitation wavelength λ, a microscope objective that receives the laser beam and focuses the laser beam in an image plane of the microscope objective, the focused laser beam being intended to illuminate a sample, an optical system for collecting a Raman scattering optical beam, and detection elements suitable for detecting the Raman scattering beam collected. More particularly, the Raman scattering microscopy apparatus further includes an adaptive optics system positioned on an optical path of the Raman scattering beam, the said adaptive optics system is configured to form the image of an energy distribution inside the confocal hole on the entrance slit of the spectrometer in such a way as to obtain an energy distribution in a direction of a height of the slit.

19 Claims, 1 Drawing Sheet

(51) Int. Cl.
  *G02B 27/00* (2006.01)
  *G02B 21/00* (2006.01)
  *G01J 3/44* (2006.01)
  *G02B 21/02* (2006.01)
  *G02B 21/16* (2006.01)

(52) U.S. Cl.
  CPC ..... *G02B 21/0064* (2013.01); *G02B 21/0076* (2013.01); *G02B 21/02* (2013.01); *G02B 21/16* (2013.01); *G02B 27/0025* (2013.01); *G01N 2021/656* (2013.01); *G01N 2201/063* (2013.01); *G01N 2201/068* (2013.01); *G01N 2201/06113* (2013.01)

(56) References Cited

OTHER PUBLICATIONS

K. J. Yi, Y. F. Lu, H. Ling, "Two-dimensional surface characterization of laser-deposited carbon films using Raman scattering", Proc. SPIE 6107, Laser-based Micropackaging, 61070O (Feb. 23, 2006).*

Girkin, John M., et al: "Adaptive optics applied to coherent anti-Stokes Raman scattering microscopy", Proceedings of SPIE, vol. 6860, Feb. 7, 2008 (Feb. 7, 2008), ISSN: 0277-786X, DOI: 10.1117/12.764445.

Booth, Martin J., et al: "Adaptive Optics for Biomedical Microscopy", OPN Optics & Phtonics News, Jan. 2012, (Jan. 2012), pp. 22-29, XP055140038, Retrieved from the Internet: URL:http://www.opticsinfobase.org/view_article.cfm?gotourl=http%3A%2F%2Fwww%2Eopticsinfobase%2Eorg%2FDirectPDFAccess%2FBC2C1F94%2DF776%2DC5A5%2DAD4994469EDF9A3B%5F226140%2Fopn%2D23%2D1%2D22%2Epdf%3Fda%3D1%26id%3D226140%26seq%3D0%26mobile%3Dno&org=.

Yi, K J, et al: "Two-dimensional surface characterization of laser-deposited carbon films using Raman scattering", Proc. of SPIE, vol. 6107, 2006, pp. 1-12, XP040219136, USA.

International Search Report, dated Jun. 15, 2015, from corresponding PCT Application.

* cited by examiner

OPTICAL MICROSCOPY SYSTEM AND METHOD FOR RAMAN SCATTERING WITH ADAPTIVE OPTICS

BACKGROUND OF THE INVENTION

Field of the Invention

The present invention relates to the field of optical microscopy or Raman microspectrometry for the analysis of material or biological samples.

In Raman microscopy, a sample is illuminated by an excitation beam, which is in general a laser beam, and the light scattered at wavelengths different than the wavelength of the excitation laser beam is observed. Raman microscopy thus differs from conventional microscopy techniques, in which the light reflected, transmitted or elastically scattered by the sample at the same wavelength as the illumination beam is observed.

Raman microscopy apparatuses exist that comprise, for example, an optical microscope, a laser source, a microscope objective and a spectrometer. The microscope objective focuses the laser beam at a focal point on the sample and forms a scattering beam. The scattering beam comprises a component called elastic scattering component or Rayleigh scattering component at the wavelength of the excitation laser, and a component called Raman scattering component at wavelengths that are different than the wavelength of the excitation laser and depend on the nature and structure of the sample. The intensity of the Rayleigh scattering is much higher than the intensity of the Raman scattering, with the intensity ratio being in general approximately $10^6$. A selective wavelength filter, for example a notch filter, allows the Raman scattering to be separated from the Rayleigh scattering in order to allow the spectrum of the Raman scattering beam to be detected and analyzed.

Raman microscopy has numerous uses in the microanalysis of materials and biochip analysis, in which a multitude of biological cells are placed in a matrix on a slide.

Adaptive optics systems are known that have optical characteristics of reflection or refraction that can be modified electronically, for example to correct the effects of certain optical disturbances or aberrations in real time. There are adaptive optics systems containing mirrors or micromirrors, in which micro-actuators allow the reflective optical surface to be directed or deformed. There are also adaptive optics systems that function via transmission, for example modulators containing liquid crystals (SLM or Spatial Light Modulator), which allow the components of a beam to be modified spatially in terms of intensity, phase and/or polarization.

Description of the Related Art

Adaptive optics systems, in particular having a deformable mirror, have been used for a number of years in astronomy, for example to correct the optical aberrations in a telescope in real time.

More recently, adaptive optics systems have been implemented in conventional optical microscopes to correct optical aberrations of the microscope itself or certain optical aberrations caused by non-uniformities in the sample.

The publication Booth, M. J., "Adaptive optics in microscopy", Phil. Trans. R. Soc. A 2007 365, 2829-843 discloses the implementation of a deformable mirror (DM) in a confocal fluorescence microscope to correct the deformations caused by the sample.

The publication Girkin, John M. et al., "Adaptive optics applied to coherent anti-Stokes Raman scattering microscopy", Proc. SPIE, vol. 6860, 2008 Feb. 7, pages 68600T-1-68600T-9, XP55139955 discloses a coherent anti-Stokes Raman scattering (CARS) microscope comprising an adaptive optics system having a deformable mirror positioned on the path of two excitation laser beams.

Moreover, the patent document US 2013/278744A1 describes a confocal optical microscopy apparatus comprising an adaptive optics device.

It is known, however, that adaptive optics systems pose certain difficulties: they are very complicated to use and require either a wavefront detector or complicated signal-processing algorithms. In general, the use of an adaptive optics system requires a very complex calibration procedure. The adaptive optics systems themselves cause optical aberrations that also need to be compensated for. In beam shaping uses, the dimension of the laser beam has to be adapted to the size of the deformable mirror, the size of the liquid lenses having an adjustable focal length or the size of the liquid crystal mirror since the resolution of the diffraction pattern on the sample depends on this dimension. Finally, transmission adaptive optics systems are configured to operate over a range of wavelengths that is rather broad but does not cover the entire spectral range from ultraviolet (UVB) to near-infrared (NIR), which is the spectral range of Raman spectrometry.

The difficulties of obtaining a satisfactory signal-to-noise ratio in a Raman microspectrometry apparatus of the prior art are known to a person skilled in the art. Thus, any additional optical system necessarily causes losses via reflection or transmission.

Certain adaptive optics systems such as phase modulation systems have the disadvantage of not being reciprocal: the phase shift caused on the forward path is not compensated for by the phase shift of the return path. It is therefore necessary to place a phase modulation system on the path of the incident laser beam and another phase modulation system on the path of the Raman beam, which doubles the difficulties and the cost of the device.

Moreover, the Raman signal is particularly sensitive to the optical materials through which it passes, and glasses sometimes introduce fluorescence or parasite peaks in the spectra, polluting the analysis of the sample.

A person skilled in the art is therefore generally discouraged from inserting an additional optical system, in particular a complex adaptive optics system, into the optical path of the excitation laser beam or the Raman scattering beam since this optical system may further reduce the signal-to-noise ratio of the Raman microspectrometry signal.

However, in general, improving the luminosity, spatial resolution and spectral resolution of a Raman scattering microspectrometry apparatus is desired in order to allow a more precise analysis of samples or allow, just like epifluorescence, Raman maps to be obtained (Raman Mapping) that have both better spatial resolution and smaller acquisition times, because of the better power densities that they bring while limiting optical aberrations.

Furthermore, a Raman microspectrometry apparatus is in general very sensitive to optical alignment defects that may appear with variations in temperature or in vibrations. There are systems for correcting the optical misalignment, based on a flat mirror, the orientation of which can be automatically adjusted according to the intensity of the Raman signal of a reference spectrum. Such a system, however, does not allow all optical alignment defects to be corrected in real time.

BRIEF SUMMARY OF THE INVENTION

In order to overcome the aforementioned disadvantage of the prior art, the present invention proposes a Raman microscopy apparatus or Raman microspectrometry apparatus comprising a laser source suitable for emitting a laser beam at an excitation wavelength A, a microscope objective suitable for receiving the laser beam and focusing the laser beam in an image plane of the microscope objective, the focused laser beam being intended to illuminate a sample, an optical system suitable for collecting a Raman scattering optical beam on the sample, detection means suitable for detecting the Raman scattering beam collected, and filtering means suitable for receiving the scattering optical beam and separating the scattering optical beam into a Rayleigh scattering beam and a Raman scattering beam.

More particularly, the invention proposes a Raman microscopy or Raman microspectrometry apparatus further comprising an adaptive optics system positioned on an optical path of the excitation laser beam, on an optical path of the Raman scattering beam or on an optical path common to the excitation laser beam and the Raman scattering optical beam.

Advantageously, the invention allows the spatial resolution (PSF or Point Spread Function) of a Raman microscopy or Raman microspectrometry apparatus to be improved and/or a better signal-to-noise ratio of the Raman scattering signal to be obtained. The invention also allows a topographical analysis of the sample to be carried out.

According to particular and advantageous aspects of various embodiments:

The Raman microscopy or Raman microspectrometry apparatus is confocal and comprises a confocal hole positioned between the microscope objective and the detection means, and said adaptive optics system is positioned on the optical path of the Raman scattering beam upstream and/or downstream of the confocal hole.

The laser beam has a Gaussian cross-section, the confocal hole has a non-circular or angular shape, and said adaptive optics system is configured to adapt the cross-section of the laser beam focused on the sample to the shape of the confocal hole, in the plane of the confocal hole.

The Raman microscopy or Raman microspectrometry apparatus further comprises a wavefront detector positioned on an optical path of the laser beam reflected by the sample, the wavefront detector is positioned in a plane optically conjugate to the image plane of the microscope objective, and the wavefront detector is suitable for detecting a position of the sample in the image plane of the microscope objective.

Said adaptive optics system comprises at least two adaptive mirrors positioned in series on the optical path of the laser beam, between the laser source and the microscope objective, said adaptive mirrors each have a variable focal length and are positioned in such a way as to form a focusing adaptive optical system having variable transverse magnification or an afocal adaptive optical system having variable magnification, and the adaptive optics system is configured to modify the diameter of the laser beam on the entrance pupil of the microscope objective according to the diameter of the entrance pupil of the microscope objective and/or according to the excitation wavelength.

Said adaptive optics system is positioned between the laser source and the image plane of the microscope objective, and the adaptive optics system is configured to spatially modulate the intensity of the laser beam in the image plane of the microscope objective.

Said adaptive optics system is configured to dynamically modulate the intensity and/or the phase and/or the polarization of the laser beam in the image plane of the microscope objective or in the pupil plane of the microscope objective, according to the sample analyzed.

The Raman scattering microscopy apparatus comprises a Raman spectrometer suitable for receiving and measuring a Raman scattering beam, said adaptive optics system is positioned on the optical path of the Raman scattering beam, between the microscope objective and the Raman spectrometer, and said adaptive optics system is configured to dynamically modulate the intensity and/or the phase and/or the polarization of the Raman scattering beam at the entrance of the Raman spectrometer in order to reduce, in the Raman signal detected, the optical aberrations such as astigmatism caused by the Raman spectrometer.

Said adaptive optics system is positioned on the optical path of the Raman scattering beam, between the confocal hole and an entrance slit of the spectrometer, and said adaptive optics system is configured to form the image of the confocal hole on the entrance slit of the spectrometer.

The invention also relates to a Raman microscopy or Raman microspectrometry method comprising the following steps:

emitting a laser beam at an excitation wavelength $\lambda$;

focusing the laser beam in an image plane of a microscope objective, the focused laser beam being intended to illuminate a sample;

collecting a scattering optical beam;

filtering the scattering optical beam in such a way as to separate said beam into an elastic scattering or Rayleigh scattering beam and a Raman scattering or fluorescence beam; and detecting the Raman scattering beam collected.

According to the invention, the method further comprises a step of modifying the optical properties of an adaptive optics system positioned on an optical path of the excitation laser beam, on an optical path of the Raman scattering beam or on an optical path common to the excitation laser beam and the Raman scattering beam in such a way as to correct all forms of aberration caused by the coupling between the microscope and the spectrometer. The Raman microscopy or Raman microspectrometry method thus allows the spatial resolution, the luminosity, the spatial distribution of the laser beam on the sample and/or the transmission of the Raman scattering beam detected to be modified.

The invention can be particularly advantageously used in apparatuses and methods for Raman microspectrometry and/or fluorescence.

The present invention also relates to the features that are mentioned in the following description, which should be considered alone or in all the technically possible combinations thereof.

BRIEF DESCRIPTION OF THE DRAWINGS

This description, given as a non-limiting example, will make it easier to understand how the invention can be carried out, with reference to the annexed drawings, in which.

DETAILED DESCRIPTION OF THE PREFERRED EMBODIMENTS

Device

Figure 1:
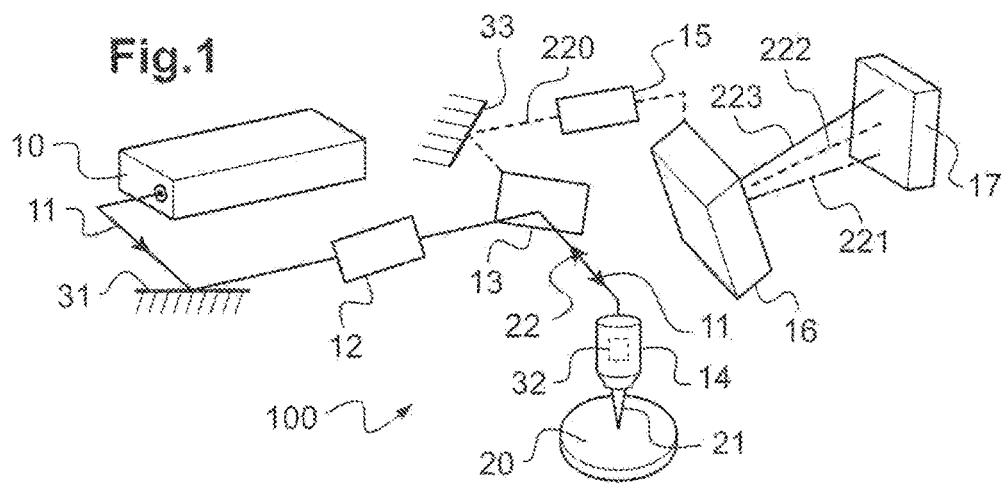
FIG. 1 schematically represents a Raman optical microspectrometry apparatus according to an embodiment of the invention.

FIG. 1 schematically represents an optical microscopy apparatus 100 of the type Raman microspectrometry apparatus. The optical microscopy apparatus 100 comprises a laser source 10, which is suitable for emitting a laser beam 11 at an excitation wavelength $\lambda$. The laser source can be chosen from a laser diode, a gas laser, a solid-state laser and a diode-pumped laser. According to the material and the type of laser, the wavelength emitted can be in the far UV (244 nm, 266 nm), in the near UV range (325 nm), in the visible range (405, 473, 532, 633, 785 and 830 nm) or in the near-infrared (1064 nm). The laser beam 11 can be continuous or pulsed, according to the type of laser source and the desired uses.

Advantageously, an optical system 12 is positioned on the optical path of the laser beam 11, between the laser source 10 and a microscope objective 14. The optical system 12 can be used to adapt the size of the laser beam to the size of the pupil of the objective via an adaptive optics variable beam expander system in order to improve the spatial resolution at the focal point and get closer to an Airy pattern. The optical system 12 can also be used to adapt the shape of the laser beam 11, which generally has circular symmetry, to a specific pupil shape, for example circular for a lens objective or annular for a Cassegrain objective, in order to prevent energy loss at the entrance of the objective, in particular in the case of a low-power beam, for example in the UV.

The microscope objective 14 receives the laser beam 11 and forms a laser beam 21 focused in the image plane of the microscope objective 14. A sample 20 is placed near the image plane of the microscope objective 14. The focused laser beam 21 thus illuminates the sample 20 at a point having a transverse dimension ideally close to the Airy pattern, or 1.22 $\lambda$/NA, where NA represents the numerical aperture of the microscope objective 14.

In a backscattering configuration as illustrated in FIG. 1, the microscope objective 14 collects a backscattered beam 22 propagating in the opposite direction with respect to the illumination laser beam.

An injection-rejection filter 13, for example a high-pass dichroic filter (edge filter) or a band-stop filter (notch filter), allows the backscattered beam 22 to be spatially separated into a Rayleigh scattering beam, at the wavelength $\lambda$ of the excitation laser beam, and a Raman scattering beam 220, which is at wavelengths different than the wavelength $\lambda$.

The confocal hole is located only on the path of the Raman scattering beam 220. An optical system 15 is positioned on the optical path of the Raman scattering beam 220, between the microscope objective 14 and the confocal hole, in order to form the image of the focused point on the confocal hole. Another optical system in general forms the image of the confocal hole on the entrance slit of a spectrometer 16. The spectrometer 16 can be a diffraction spectrometer or a dispersive spectrometer. The spectrometer 16 spatially separates the Raman scattering beam 220 into various spectral components 221, 223, 223. A detector 17 detects the intensity of one or more spectral components 221, 222, 223 according to the wavelength or the Raman frequency. An analysis system then allows the spectral components 221, 222, 223 to be processed and analyzed in order to deduce an analysis of the sample 20 therefrom.

In a transmission configuration (not shown), an optical system collects a beam that is scattered through the sample and propagates in the same direction as the illumination laser beam.

Finally, in another configuration, the scattering beam is collected in a direction transverse to the direction of the excitation laser beam.

Advantageously, the same single microscopy or microspectrometry apparatus can be configured to allow the measurement of both backscattering and forward scattering and/or transverse scattering.

Moreover, in a known way, in certain embodiments of scanning microscopy, the microscopy apparatus further comprises means for angular displacement of the laser beam, consisting for example of a scanner having one or two axes, wherein the focused laser beam scans an area on the surface of the sample. The laser scanning allows a Raman image having microscopic resolution to be created. In other uses, the signal is integrated during the scanning by the laser beam in order to average the Raman signal over an area of the sample.

The Raman microscopy apparatus 100 illustrated in FIG. 1 comprises at least one adaptive optics system 31, 32 and/or 33.

The adaptive optics system 31 is positioned between the laser source 10 and the injection-rejection filter 13, only on the optical path of the excitation laser beam 11. In the example illustrated in FIG. 1, the adaptive optics system 31 is an optical system that operates via reflection, for example an adaptive mirror optical system.

The adaptive optics system 32 is positioned between the injection-rejection filter 13 and the microscope objective 14, on the optical path common to the excitation laser beam 11 and the scattering beam 22, which comprises both the Rayleigh scattering and the Raman scattering. In the example illustrated in FIG. 1, the adaptive optics system 32 is an optical system that operates via transmission, for example a spatial light modulator, or SLM.

The adaptive optics system 33 is positioned between the injection-rejection filter 13 and the spectrometer 16, only on the optical path of the Raman scattering beam 220. In the example illustrated in FIG. 1, the adaptive optics system 33 is an optical system that operates via reflection, for example an adaptive mirror optical system.

The adaptive optics systems 31, 32 and 33 can be used independently of one another, combined in pairs, or all together.

The position, number and type of adaptive optics systems on the various optical paths advantageously allows a function associated with one of the adaptive optics systems to be selected or the functions of a plurality of adaptive optics systems to be combined.

An adaptive optics system 31, 32, 33 can be used to correct optical aberrations in the microspectrometry apparatus and/or in the sample, according to the use.

Figure 3:
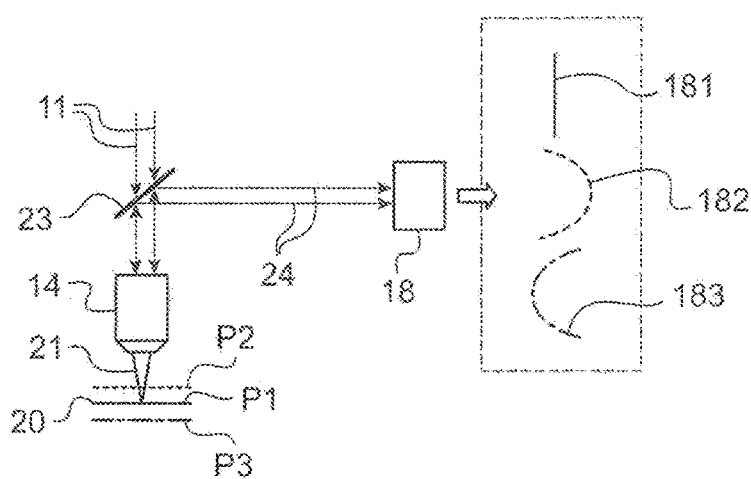
FIG. 3 illustrates an autofocus system in an optical microscopy apparatus according to a specific embodiment of the invention.
Figure 2:
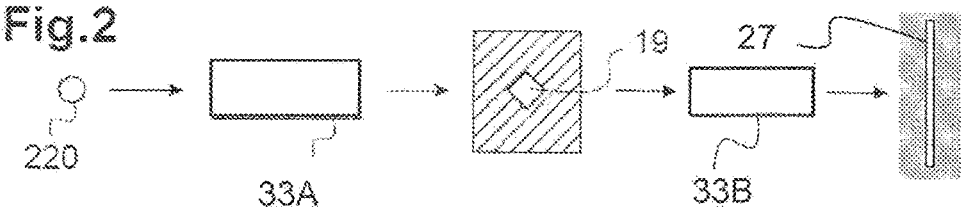
FIG. 2 schematically represents an adaptive optics system configured to form the image of a Gaussian laser beam on a confocal hole according to an embodiment of the invention.
Figure 4:
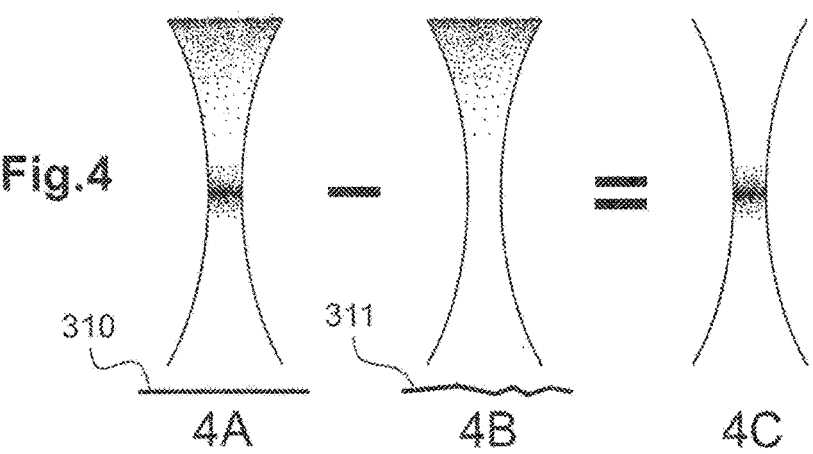
FIG. 4 schematically represents an adaptive optics system configured to correct the wavefront of the excitation laser beam according to another embodiment of the invention.

We will describe several embodiments in detail, in particular in relation to FIGS. 2-4.

FIG. 2 schematically illustrates a first embodiment, in which an adaptive optics system 33 is positioned in a confocal Raman microscope. In general, in Raman microspectrometry, a confocal hole 19 having an overall non-circular shape is used, for example having the shape of a rhombus for Raman microspectrometry or having the shape of a hexagon in fluorescence microscopy. The confocal hole 19 is made in an opaque substrate. The laser beam 11 from the laser source, however, is in general a Gaussian beam having a circular cross-section. In general, the Raman scattering beam 220 also has a cross-section having rotational symmetry about the optical axis.

In the prior art, a conventional optical system having lenses or mirrors forms the image of the waist of the Raman beam in the plane of the confocal hole 19 in such a way that the diameter of the laser beam 11 covers the totality of the surface of the confocal hole 19. This image formation leads to losses in the intensity of the laser beam via vignetting at the edges of the confocal hole 19 when only luminosity and not confocality is desired, with the hole open to a maximum.

In the advantageous specific first embodiment, an adaptive optics system 33A is used, and this system is configured to form the image for analyzing the sample in the plane of the confocal hole in the plane of the confocal hole 19 and adapt the shape of the beam to the shape of the confocal hole 19. In one embodiment, the adaptive optics system 33A consists of an adaptive optics mirror located only on the Raman scattering path. This adaptive optics mirror modifies the phase or the intensity of the incident field to model the shape of the beam on the hole differently from the shape of the beam exiting the source. For example, in certain cases, when the hole has the same size as the image at the focal point 21, which has the advantage of not inducing any signal losses but leads to low confocality, an energy distribution in the shape of a rhombus is therefore generated. In another example, an energy distribution having an elliptical shape is generated inside the confocal hole, which is open wide and imaged on the entrance slit of the spectrometer in such a way as to obtain an energy distribution in the direction of the height of the slit, without vignetting on the entrance slit of the spectrometer.

In a variant of this first embodiment, another adaptive optics system 33B is positioned between the confocal hole 19 and the entrance slit 27 of the spectrometer, on the optical path of the Raman scattering beam 220. Advantageously, another adaptive optics system 33B forms the image of the Raman scattering beam 220 on the entrance slit 27 of the spectrometer. For example, the adaptive optics system 33B is configured to adapt the rhombus shape of the confocal hole to the elongated rectangular shape of the entrance slit 27 of the spectrometer in order to maximize the intensity of the Raman scattering signal detected. In another example, the adaptive optics system 33B is configured to adapt the circular or elliptical shape of the Raman scattering beam 220 to the elongated rectangular shape of the entrance slit 27 of the spectrometer.

This first embodiment provides a gain in the luminosity of the Raman scattering beam and also allows realignment on the hole and/or on the entrance slit of the spectrometer, even though the confocality properties are relatively low.

FIG. 3 schematically illustrates a variant of a Raman microscopy or Raman microspectrometry apparatus further comprising an auto-focusing or autofocus device.

In the microscopy apparatuses of the prior art, the autofocus device generally comprises a pinhole and a sensor such as a photodiode. A beam splitter or beam splitter cube transmits a portion of the laser beam to the microscope objective 14 and sends a portion of the laser beam reflected by the surface of the sample, in general 10%, to the pinhole. The pinhole, having a diameter of 100 microns for example, is positioned in a plane optically conjugate to the image plane of the microscope objective. The sensor is positioned behind the pinhole. A lens focuses the image of the sample surface onto the photodiode. The focal length of the lens is defined in such a way as to have sufficient magnification for good resolution on Z (axis of the beam) and therefore good precision of the autofocus. In general, a micrometric motorized system allows relative axial movement between the sample and the microscope objective. The sensor detects the intensity of the reflected signal according to this axial movement. The maximum intensity detected by the photodiode indicates the position of the reflective surface of the sample in the image plane of the objective. An automatic autofocus system thus allows the relative axial movement of a sample-carrying stage and the acquisition of the signal reflected onto the sensor to be controlled in such a way as to place the sample in the focal plane of the microscope objective. Such an autofocus device and method, however, are not sensitive to the direction of the defocus since the intensity of the reflected beam generally decreases symmetrically on either side of the image plane. At least one movement there and back around the image plane is necessary. The autofocus devices and methods are thus in general rather slow and sometimes converge with difficulty since perfect alignment is required, in particular when starting from an initial position of the sample distant from the image plane of the microscope objective.

FIG. 3 illustrates a detail of a Raman scattering microscopy apparatus, and more specifically, an autofocus device in such a microscopy apparatus. FIG. 3 shows the microscope objective 14, the image plane (or focal plane) P1 of the microscope objective 14, a plane P2 located between the microscope objective and the image plane P1, and a plane P3 located beyond the image plane P1.

A beam splitter 23, for example a beam splitter having a coefficient of reflection of 10% and a coefficient of transmission of 90%, transmits the laser beam 11 to the microscope objective 14 and sends a portion 31 of the laser beam reflected by the surface of the sample to a wavefront detector 18, for example a Shack-Hartmann sensor or camera. The analysis of the reflected beam allows, for example, the signal to be decomposed into Zernike polynomials.

The second polynomial $Z^2_0$ is of particular interest. When the reflective surface of the sample is in the image plane P1, a wavefront signal 181 having a determined shape, for example flat, is detected. When the reflective surface of the sample is in the image plane P2, a wavefront signal 182, which has a curve with respect to the signal 181, is detected. When the reflective surface of the sample is in the image plane P3, a wavefront signal 183, which has another curve with respect to the wavefront signal 181, in the direction opposite the direction of the curve of the wavefront signal 182, is detected. The wavefront detector thus allows the position of the sample in the image plane P1 of the microscope objective to be detected in a more precise and faster manner.

Moreover, the analysis of a Zernike mode (the second polynomial $Z^2_0$) allows a change in the direction of the curve of the wavefront to be detected, thus allowing the direction of the defocus of the sample with respect to the image plane P1 to be detected. The autofocus algorithm can therefore converge faster than with an intensity sensor.

As an alternative or complement, other Zernike modes could be used. Thus, the first Zernike mode can allow an analysis of whether or not the sample is inclined.

More generally, the use of adaptive optics and a wavefront detector allows Raman spectrometry to be combined with a surface topography technique.

Another advantageous specific embodiment uses an adaptive optics system comprising two adaptive optical components operating via transmission or reflection, for example a mirror having a deformable membrane, or a system of ×2 liquid lenses positioned in series on the optical path of the laser beam 11. The two adaptive optical components are positioned in such a way as to form an afocal adaptive optical system. In this embodiment, the two adaptive optical components are configured to have radii of curvature different from each other in order to form an adaptive optical system, for example an afocal system having a magnification other than 1.

In a first variant, the adaptive optical system can be modified in such a way that the focal length of one or both of the mirrors varies while preserving an afocal system arrangement, in order to form an afocal optical system having variable magnification, preferably greater than 1.

Such an afocal adaptive optical system has various uses.

In a first use, the variable-magnification afocal adaptive optical system is positioned on the optical path of the laser beam 11 between the laser source 10 and the microscope objective 14 or on the common path. The two focal lengths of the two adaptive optical components vary jointly, which allows the size of the laser at the pupil of each objective to be adapted regardless of the wavelength. This system improves the spatial resolution in order to reach the diffraction limit (Airy pattern).

The variable magnification of the adaptive optics system allows a variable beam expander to be formed. This adaptive optics system allows the diameter of the laser beam to be adapted to the diameter of the pupil of the objective, thus limiting the losses in intensity in the excitation laser beam. Such a variable-magnification afocal adaptive optics system allows the excitation laser to be changed, for example in order to change the wavelength λ, while optimizing the transfer of intensity from the laser source to the microscope objective.

In another variant, the adaptive optical system can be modified in such a way that the focal length of one or both of the mirrors varies, in order to form a focusing optical system having variable transverse magnification.

In another use, the adaptive optical system is positioned only on the common path. Then, the adaptive optical system is willfully misadjusted in such a way as to converge on the objective pupil and thus illuminate a greater area of the sample. This configuration allows areas of interest to be quickly located via imaging by matrix camera and a Raman analysis to be carried out on these areas of interest after a cursory examination. This configuration eliminates the need to scan the entire surface of the sample in order to locate an area of interest.

In another advantageous specific embodiment, an adaptive optics system 31 positioned on the optical path of the laser beam between the laser source 10 and the microscope objective 14 is used to modify the spatial distribution of energy of the beam focused on the sample 20.

In a particularly advantageous manner, software for morphological recognition of particles (such as the "particle finder" software module provided as an option with the Raman analysis software LabSpec6 from HORIBA) is coupled with an adaptive optics system in order to spatially structure the shape of the laser according to the shape of the particle to be analyzed.

For example, a phase-modulation adaptive optical system (spatial light modulator) calculates the Fourier transform of an image, for example an image of the sample with particles, and imposes this hologram onto the liquid-crystal phase-modulation adaptive optical system. After reflection of the laser beam on this phase-modulation adaptive optical system, the beam at the output of the phase-modulation adaptive optical system reproduces the initial image (cf. the article "Holographic analysis of caged neurotransmitter", NATURE METHODS|VOL. 5 NO. 9|SEPTEMBER 2008), or even better, re-images the illuminated particles along the direction of the height of the entrance slit of the spectrometer, which allows a plurality of particles to be analyzed at the same time via a single CCD reading.

The difficulty resides in the fact that a second adaptive optics system that recombines all the illuminated particles at the same time in the single confocal hole is required on the Raman scattering path (the first being located only on the laser path). Indeed, a single phase-modulation adaptive optics system on the common path would not function since such an adaptive optics system is not reversible, and the phase changed on the forward path would be doubled on the return path instead of being compensated for. The advantage of this embodiment is that only the area of interest is illuminated, without illuminating the surrounding area, which would be detrimental to the signal-to-noise ratio.

This embodiment allows unwanted areas on the sample to be avoided, concentrating the energy of the laser beam only on the useful portion of the optical field. Unwanted signals from the surrounding particles or from the substrate are thus eliminated.

In another variant, the adaptive optics system 31 is used to correct the spatial distribution of the wavefront of the laser in order to reduce the spatial extent of the laser beam at the focal point (or PSF for point spread function) and/or to correct optical aberrations, in particular caused by the variations in index in the sample itself, in order to improve the spatial resolution of the microscopy apparatus.

FIG. 4 illustrates an example of wavefront correction in the excitation laser beam. FIG. 4A shows a longitudinal cross-section of the laser beam 11 around the waist, that is to say, around the focusing area. In the absence of a deformation of the adaptive optics system 310, the laser beam comprises disturbances caused by optical aberrations caused by the microscopy apparatus and/or by the sample. FIG. 4B shows the effect of a deformation 311 of the adaptive optics system, which is configured to compensate for the disturbances of the wavefront of the laser beam. The adaptive optics system 31 thus configured allows the disturbances of the laser beam to be eliminated (FIG. 4C). This embodiment thus allows the spatial resolution at the focal point of the laser beam to be improved.

In another embodiment, an adaptive optics system 33 is positioned between the filter 13 and the spectrometer 16, on the optical path of the Raman scattering beam 22. Advantageously, the adaptive optics system 33 is configured to compensate for optical aberrations in the spectrometer. Thus, for example, the defect of astigmatism is corrected by modulating the beam as would be done by a cylindrical lens, which decomposes the sagittal and tangential planes and only modifies one of these planes. A radius of curvature is created in a single direction of the adaptive optics mirror, without affecting the other direction. This embodiment allows a cylindrical lens with a variable focal length in a single direction to be created in order to compensate for the amplitude of the astigmatism defect.

More particularly, the adaptive optics system 33 is configured to compensate for the astigmatism defect caused by the mirrors of the spectrometer, in order to eliminate the astigmatism defects on the detector 17 while obtaining better density in the energy detected. For example, the adaptive optics system 33 is controlled in such a way that said system introduces an astigmatism defect that is the inverse of the defect of the spectrometer 16 before the entrance slit of the spectrometer.

The lines of a spectrum correspond to points imaged with a CCD detector. In order for the lines to be fine (good spectral resolution), the concave mirrors inside the spectrometer are drawn in such a way as to have image points on the CCD that are as fine as possible. Vertical elliptical points are thus obtained, and there is therefore a loss in terms of height. By creating a CCD image of the spot on the detector, this astigmatism defect can be visualized very well, and this defect is partly corrected by placing a cylindrical lens, which compensates for this defect, before the slit, creating the inverse defect.

This embodiment eliminates the need to use a unique passive optics system dedicated to each spectrometer 16.

In another embodiment, one or more adaptive optics components are used in a Raman microscopy apparatus in order to automatically stabilize the optical alignment of the Raman microscopy apparatus with respect to temperature variations or vibrations, and also stabilization of the focus on the sample. Thus, a control spectrum is acquired with a reference sample in particular conditions in order to obtain an indication of the overall state of the instrument. For highly dispersive systems (which corresponds in general to a large apparatus with a long focal length) subject to dilatations, adaptive optics are used to compensate for signal loss without losing the highly precise factory alignment. In this case, more so than a function of improving performance, the adaptive optics have a function of maintaining the quality of an apparatus.

The invention claimed is:

1. A Raman microscopy or Raman microspectrometry apparatus of confocal type, said apparatus comprising:
    a laser source suitable for emitting a laser beam at an excitation wavelength λ;
    a microscope objective suitable for receiving the laser beam and focusing the laser beam in an image plane of the microscope objective, the focused laser beam being intended to illuminate a sample;
    an optical system suitable for collecting a scattering optical beam on the sample;
    a filter suitable for receiving the scattering optical beam and separating the scattering optical beam into a Rayleigh scattering beam and a Raman scattering beam;
    a detection system comprising a spectrometer suitable for detecting and measuring the Raman scattering beam collected;
    a confocal hole positioned between the microscope objective and the detection system; and
    an adaptive optics system positioned on an optical path of the Raman scattering beam,
    wherein said adaptive optics system is configured to form the image of an energy distribution inside the confocal hole on the entrance slit of the spectrometer in such a way as to obtain an energy distribution in a direction of a height of the slit.

2. The Raman microscopy or Raman microspectrometry apparatus according to claim 1, wherein said adaptive optics system is positioned on the optical path of the Raman scattering beam upstream and/or downstream of the confocal hole.

3. The Raman microscopy or Raman microspectrometry apparatus according to claim 2, wherein the laser beam has a Gaussian cross-section, the confocal hole has a non-circular or angular shape, and comprising further another adaptive optics system positioned on an optical path of the laser beam, said another adaptive optics system being configured to adapt the cross-section of the laser beam focused on the sample to the shape of the confocal hole, in the plane of the confocal hole.

4. The Raman microscopy or Raman microspectrometry apparatus according to claim 3, wherein said another adaptive optics system comprises at least two adaptive mirrors positioned in series on the optical path of the laser beam, between the laser source and the microscope objective, said at least two adaptive mirrors each have a variable focal length and are positioned in such a way as to form a focusing adaptive optical system having variable magnification or an afocal adaptive optical system having variable magnification, and the another adaptive optical system is configured to modify the diameter of the laser beam on the entrance pupil of the microscope objective according to the diameter of the entrance pupil of the microscope objective.

5. The Raman microscopy or Raman microspectrometry apparatus according to claim 4, wherein said adaptive optics system is positioned between the laser source and the image plane of the microscope objective, and the adaptive optics system is configured to spatially modulate the intensity of the laser beam in the image plane of the microscope objective.

6. The Raman microscopy or Raman microspectrometry apparatus according to claim 4, further comprising a spectrometer suitable for receiving and measuring a Raman scattering beam, wherein said adaptive optics system is positioned on the optical path of the Raman scattering beam, between the microscope objective and the spectrometer, and said adaptive optics system is configured to dynamically modulate the intensity and/or the phase of the Raman scattering beam at the entrance of the spectrometer in order to reduce, in the Raman signal detected, the optical aberrations such as astigmatism caused by the spectrometer.

7. The Raman microscopy or Raman microspectrometry apparatus according to claim 3, wherein said another adaptive optics system is positioned between the laser source and the image plane of the microscope objective, and the adaptive optics system is configured to spatially modulate the intensity of the laser beam in the image plane of the microscope objective.

8. The Raman microscopy or Raman microspectrometry apparatus according to claim 7, wherein said another adaptive optics system is configured to dynamically modulate the intensity and/or the phase of the laser beam in the image plane of the microscope objective or in the pupil plane of the microscope objective, according to the sample analyzed.

9. The Raman microscopy or Raman microspectrometry apparatus according to claim 7, further comprising a spectrometer suitable for receiving and measuring a Raman scattering beam, wherein said adaptive optics system is positioned on the optical path of the Raman scattering beam, between the microscope objective and the spectrometer, and said adaptive optics system is configured to dynamically modulate the intensity and/or the phase of the Raman scattering beam at the entrance of the spectrometer in order to reduce, in the Raman signal detected, the optical aberrations such as astigmatism caused by the spectrometer.

10. The Raman microscopy or Raman microspectrometry apparatus according to claim 3, further comprising a wavefront detector positioned on an optical path of the laser beam reflected by the sample, wherein the wavefront detector is positioned in a plane optically conjugate to the image plane of the microscope objective, and the wavefront detector is suitable for detecting a position of the sample in an image plane of the microscope objective.

11. The Raman microscopy or Raman microspectrometry apparatus according to claim 3, wherein said adaptive optics system comprises at least two adaptive mirrors positioned in series on the optical path of the laser beam, between the laser source and the microscope objective, said at least two adaptive mirrors each have a variable focal length and are positioned in such a way as to form a focusing adaptive optical system having variable magnification or an a focal adaptive optical system having variable magnification, and the adaptive optical system is configured to modify the diameter of the laser beam on the entrance pupil of the microscope objective according to the diameter of the entrance pupil of the microscope objective.

12. The Raman microscopy or Raman microspectrometry apparatus according to claim 3, wherein said adaptive optics system is positioned between the laser source and the image plane of the microscope objective, and the adaptive optics system is configured to spatially modulate the intensity of the laser beam in the image plane of the microscope objective.

13. The Raman microscopy or Raman microspectrometry apparatus according to claim 3, further comprising a spectrometer suitable for receiving and measuring a Raman scattering beam, wherein said adaptive optics system is positioned on the optical path of the Raman scattering beam, between the microscope objective and the spectrometer, and said adaptive optics system is configured to dynamically modulate the intensity and/or the phase of the Raman scattering beam at the entrance of the spectrometer in order to reduce, in the Raman signal detected, the optical aberrations such as astigmatism caused by the spectrometer.

14. The Raman microscopy or Raman microspectrometry apparatus according to claim 1, further comprising a wavefront detector positioned on an optical path of the laser beam reflected by the sample, wherein the wavefront detector is positioned in a plane optically conjugate to the image plane of the microscope objective, and the wavefront detector is suitable for detecting a position of the sample in an image plane of the microscope objective.

15. The Raman microscopy or Raman microspectrometry apparatus according to claim 14, wherein said adaptive optics system comprises at least two adaptive mirrors positioned in series on the optical path of the laser beam, between the laser source and the microscope objective, said at least two adaptive mirrors each have a variable focal length and are positioned in such a way as to form a focusing adaptive optical system having variable magnification or an afocal adaptive optical system having variable magnification, and the adaptive optical system is configured to modify the diameter of the laser beam on the entrance pupil of the microscope objective according to the diameter of the entrance pupil of the microscope objective.

16. The Raman microscopy or Raman microspectrometry apparatus according to claim 14, wherein said adaptive optics system is positioned between the laser source and the image plane of the microscope objective, and the adaptive optics system is configured to spatially modulate the intensity of the laser beam in the image plane of the microscope objective.

17. The Raman microscopy or Raman microspectrometry apparatus according to claim 14, further comprising a spectrometer suitable for receiving and measuring a Raman scattering beam, wherein said adaptive optics system is positioned on the optical path of the Raman scattering beam, between the microscope objective and the spectrometer, and said adaptive optics system is configured to dynamically modulate the intensity and/or the phase of the Raman scattering beam at the entrance of the spectrometer in order to reduce, in the Raman signal detected, the optical aberrations such as astigmatism caused by the spectrometer.

18. The Raman microscopy or Raman microspectrometry apparatus according to claim 1, wherein said adaptive optics system is configured to dynamically modulate the intensity and/or the phase of the Raman scattering beam at the entrance of the spectrometer in order to reduce, in the Raman signal detected, the optical aberrations such as astigmatism caused by the spectrometer.

19. A Raman microscopy or Raman microspectrometry method comprising the following steps:
   emitting a laser beam at an excitation wavelength $\lambda$;
   focusing the laser beam in an image plane of a microscope objective, the focused laser beam being intended to illuminate a sample;
   collecting a scattering optical beam;
   filtering the scattering optical beam in such a way as to separate said beam into an elastic scattering or Rayleigh scattering beam and a Raman scattering or fluorescence beam;
   filtering by a confocal hole; and
   detecting the Raman scattering beam collected on an entrance slit of the spectrometer,
   wherein the method further comprises a step of:
   modifying the optical properties of an adaptive optics system positioned on an optical path of the Raman scattering beam in such a way as to form an image of an energy distribution inside the confocal hole on the entrance slit of the spectrometer in such a way as to obtain an energy distribution in a direction of a height of the slit.

* * * * *